(12) United States Patent
Hofmann

(10) Patent No.: US 6,801,317 B2
(45) Date of Patent: Oct. 5, 2004

(54) PLASMON RESONANCE SENSOR

(75) Inventor: Andreas Hofmann, Wallenfels (DE)

(73) Assignee: Jandratex GmbH, Wallenfels (DE)

( * ) Notice: Subject to any disclaimer, the term of this patent is extended or adjusted under 35 U.S.C. 154(b) by 0 days.

(21) Appl. No.: 10/275,164

(22) PCT Filed: May 9, 2001

(86) PCT No.: PCT/EP01/05287
§ 371 (c)(1),
(2), (4) Date: Nov. 1, 2002

(87) PCT Pub. No.: WO01/86262
PCT Pub. Date: Nov. 15, 2001

(65) Prior Publication Data
US 2003/0076501 A1 Apr. 24, 2003

(30) Foreign Application Priority Data
May 12, 2000 (DE) .......................... 100 23 363

(51) Int. Cl.⁷ ............................................. G01N 21/55
(52) U.S. Cl. ...................................................... 356/445
(58) Field of Search ................................ 356/445, 318, 356/343, 417, 446, 246; 250/458.1, 459.1, 461.1, 461.2

(56) References Cited

U.S. PATENT DOCUMENTS

| | | | |
|---|---|---|---|
| 4,844,613 A | | 7/1989 | Batchelder et al. |
| 5,255,075 A | * | 10/1993 | Cush .......................... 356/445 |
| 5,313,264 A | * | 5/1994 | Ivarsson et al. ............... 356/73 |
| 5,485,277 A | * | 1/1996 | Foster .......................... 356/445 |
| 5,917,607 A | * | 6/1999 | Naya ........................... 356/445 |
| 5,965,456 A | * | 10/1999 | Malmqvist et al. .......... 436/514 |
| 5,991,048 A | | 11/1999 | Karlson et al. |
| 5,999,262 A | * | 12/1999 | Dobschal et al. ............ 356/456 |
| 6,570,657 B1 | * | 5/2003 | Hoppe et al. ................ 356/445 |
| 2002/0126290 A1 | * | 9/2002 | Naya ........................... 356/445 |
| 2002/0145737 A1 | * | 10/2002 | Kubo et al. .................. 356/445 |

FOREIGN PATENT DOCUMENTS

| | | |
|---|---|---|
| DE | 198 14 811 C | 8/1999 |
| EP | 0 971 226 A | 1/2000 |

OTHER PUBLICATIONS

Patent Abstracts of Japan vol., 1998, No. 05, Apr. 30, 1998 & JP 10 019769 A. Jan. 23, 1998.

* cited by examiner

Primary Examiner—Michael P. Stafira
(74) Attorney, Agent, or Firm—Michael J. Striker

(57) ABSTRACT

The invention relates to a plasmon resonance sensor that comprises collimator optics (13) in the form of a cylindrical lens that is interposed between the laser diode (7) and the prism (1), said prism being provided with a reflective metal layer (5). This arrangement preserves the beam divergence in the plane of incidence that comprises all angles of incidence that are potentially possible for a resonance and that are detected by the detector (8). In a plane perpendicular to the plane of incidence the beam path is collimated, thereby allowing for a compact design and for the simultaneous arrangement of a plurality of measuring cells that are arranged perpendicular to the plane of incidence one behind the other.

9 Claims, 2 Drawing Sheets

PLASMON RESONANCE SENSOR

BACKGROUND OF THE INVENTION

The invention relates to a plasmon resonance sensor for biological, biochemical or chemical tests, with an optically transparent body, in particular a glass prism, a reflective metal layer or semiconductor layer which is applied to one face of the body and has a surface sensitive to molecules to be detected in a sample, which forms a measurement cell in conjunction with a cuvette, a monochromatic light source, in particular a laser diode, for emitting a divergent light pencil or beam path through the optically transparent body onto the inner face of the layer, and a detector which is assigned to the emerging beam path reflected by the layer and registers as a function of time the light emergence angle, which changes as a result of molecule buildup on the sensitive surface, at which an emerging light intensity minimum occurs owing to resonance.

Such a plasmon resonance sensor, with a glass prism, a thin gold layer of from 40 to 70 nm and a light source in the form of a laser diode, is known from U.S. Pat. No. 4,844,613.

The phenomenon of surface plasmon resonance (SPR) involves collective excitation of the electrons at the surface of a layer which has free electrons. The resonant frequency of the surface plasmons is very sensitive to the refractive index of the medium which is adjacent to the sensitive surface. This can be used in order to analyze thin layers (refractive index or layer thickness). Especially in biosensor technology, this effect is used in order to study the buildup kinetics of biomolecules on a functionalized metal surface. To that end, the resonance condition of the surface plasmons is detected in a temporally resolved fashion. The surface plasmons of the thin metal layer are excited by light which shines through the glass onto the metal layer at a particular angle or in a particular angle range. The resonance condition is then satisfied for a particular combination of wavelength and angle of incidence. Under this resonance condition, the intensity of the light reflected from the metal layer is reduced significantly owing to the generation of surface plasmons. In order to find the resonance condition, it is possible to scan either the angle of incidence (at constant wavelength) or the wavelength (at constant angle of incidence), and to detect the intensity of the reflected light.

In the plasmon resonance sensor described in the introduction, it is necessary to operate with a fixed wavelength and to determine the angle of incidence for which the resonance condition is satisfied. In this case, a laser diode which emits an elliptical beam cone is used. The aperture angles are typically 22° in one dimension and 9° in the other dimension—in each case at half of the intensity maximum (FWHM). This beam divergence is used in order, without any beam shaping optics and without any change in the alignment of the light source in relation to the reflective layer, to illuminate the latter with light at different angles of incidence within an angle range which is compatible with achieving the resonance condition. Accordingly, an elongate detector arrangement is provided, which picks up the divergent emerging beam path over its full extent in the light incidence plane, and can hence determine the angle of incidence for which the resonance condition is satisfied at the time of measurement.

Since it makes do without beam shaping optics and devices for changing the angle of incidence of the light, this known plasmon resonance sensor has a comparatively simple design and is therefore economical to manufacture. However, light beams with a different angle of incidence strike different points on the reflective metal layer, so that the uniformity of the latter must be subject to stringent requirements in order to prevent falsification of the measurement results. Nevertheless, it is possible to apply metal layers which are sufficiently uniform in this sense.

The essential disadvantage of the known design is therefore the fact that the plasmon resonance sensor, which is equipped with a single measurement cell, has a low performance in terms of the number of tests which can be carried out, and it does not permit any simultaneous reference measurements in order to eliminate the effect, for example, of the reflective metal layer becoming heated. Indeed, it is precisely because of the strong temperature dependence of the refractive index of liquids, and since the samples to be studied are normally studied when they are dissolved in liquid, that reference measurements are particularly useful. It should also be noted in this context that, owing to the divergent beam path, any additional measurement cells need to be arranged at a large distance from one another, so as to avoid overlap between different beam cones and therefore falsifications. Such a spacing, however, would conflict with the desired compact configuration and also significantly increase the costs for correspondingly large components.

It is already known from EP 305 109 B1, in the case of a comparable plasmon resonance sensor for carrying out biological tests, to operate with a parallel-radiating light source and to generate therefrom, by means of optics, a convergent beam fan with all the required angles of incidence, with optics that restore parallel alignment of the beam path before it strikes the detector also being provided in the divergent emerging beam path. In this plasmon resonance sensor, the light is focused onto one point on the metal layer, so that the effect of nonuniformities of the metal layer is substantially eliminated. The drawback of this, however, is that it is necessary to tolerate increased heating of the metal layer and results which are thereby falsified. Another disadvantage of the known plasmon resonance sensor involves the comparatively expensive beam shaping optics. Moreover, additional measurement cells to increase performance and for reference measurements would also require additional corresponding beam shaping optics, and they hence make the plasmon resonance sensor significantly more expensive.

SUMMARY OF THE INVENTION

It is therefore an object of the invention to provide a plasmon resonance sensor which permits high test performance with simultaneously error-free results, while having a compact and inexpensive design.

On the basis of the plasmon resonance sensor described in the introduction, this object is achieved according to the invention by the fact that collimation optics, which collimate the incident beam path perpendicularly to the incidence plane but still leave it divergent in the incidence plane, are arranged between the light source and the optically transparent body.

Expedient refinements and developments of the invention are given in the dependent claims.

The plasmon resonance sensor according to the invention makes do with simple beam shaping optics in the form of a cylindrical lens, and it hence requires only minor equipment outlay. Although the original beam divergence, for example of a laser diode, is used in order to cover the full appropriate range of angles of incidence, the intentional parallel alignment of the beam path in a direction perpendicular to the incidence plane provides a narrow beam path in this direction, which permits compact side-by-side arrangement of a plurality of equivalent plasmon resonance sensors, and therefore of a plurality of measurement cells, and this leads to a high-performance device with the opportunity for advantageous reference measurements.

Expediently, however, this result is achieved not by sequential arrangement of a plurality of complete plasmon resonance sensors, but instead by arranging two or more measurement cells for different samples, which are aligned in a row perpendicularly to the incidence plane, on a common optically transparent body or prism, with each measurement cell being assigned its own detector. Such a design with a common optically transparent body or prism, and optionally only one light source and single collimation optics, leads to a particularly low cost outlay in terms of performance.

Exemplary embodiments of the invention will be explained in more detail below with the aid of a schematic drawing, in which.

DETAILED DESCRIPTION OF THE PREFERRED EMBODIMENTS

Figure 1:
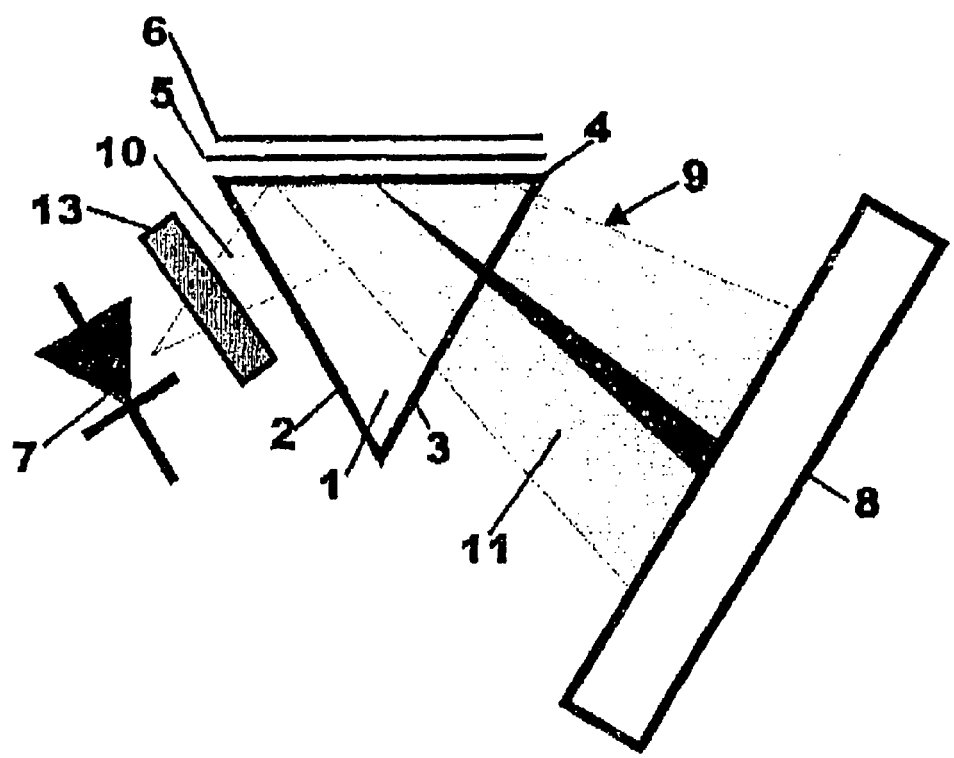
FIG. 1 shows a plasmon resonance sensor in side view.

According to FIG. 1, an optically transparent body 1 in the form of a glass prism with a triangular cross-sectional shape is provided. This prism has a light incidence side 2, a light exit side 3 and a horizontally aligned upper reflection side 4. A reflective metal layer 5, which, for example, consists of gold with a thickness of 50 nm, is applied to this reflection side 4. A sensitive coating 6 is furthermore applied to the metal layer 5, as schematically indicated. This sensitive coating is, for example, matched to biomolecules to be detected in the sample to be studied, so that the relevant biomolecules build up on the sensitive coating. Such coatings and their regeneration, for example by means of a hydrochloric acid solution, are well known to the person skilled in the art.

The light incidence side 2 is assigned a monochromatic light source 7 in the form of a laser diode, and, accordingly, a detector 8 faces the light exit side 3 of the prism 1, at a distance therefrom. Hence, as represented in FIG. 1, the laser diode 7 generates a divergent beam path 9 which is reflected by the metal layer 5 and directed onto the detector 8. The beam path 9 is divided into an incident beam path 10 in front of the metal layer 5 and an emerging beam path 11 behind the metal layer 5, the incidence plane 12 (FIG. 2) extending parallel to the drawing plane of FIG. 1.

Collimation optics 13 are arranged in the incident beam path 10 in the form of a cylindrical lens, which is arranged inclined in the incidence plane 12 in accordance with the incident beam path. This cylindrical lens 13 causes collimation or parallel alignment of the light beams only in a direction perpendicular to the incidence plane 12 (FIG. 2), while the beam divergence is preserved in the incidence plane, as shown by FIG. 1. Owing to the action of the collimation optics 13, the beam path 9 extends through the prism 1 within a comparatively narrow range with a small extent perpendicular to the incidence plane 12.

The plasmon resonance taking place, on which the test method carried out with the plasmon resonance sensor according to the invention is based, is schematically indicated in FIG. 1. The divergence of the beam path 9 in the incidence plane 12 is large enough to cover the range of angles of incidence within which the resonance phenomenon occurs. Specifically, the angle of incidence leading to resonance changes owing to the buildup of molecules from the sample to be studied onto the sensitive coating 6. At the angle of incidence respectively corresponding to resonance, the emerging light beam is significantly attenuated, and this angle of incidence is registered by the detector 8 in a temporally resolved fashion. Accordingly, levels or regions with different light intensity are indicated in FIG. 1 on the emerging beam path 11, with the most heavily darkened region corresponding to the weakest emergence of light and therefore to the time-dependent sample-specific angle of incidence for resonance. According to FIG. 1, the resonance hence takes place at a central angle of incidence. The conditions explained with reference to FIG. 1 apply in general to all the exemplary embodiments described below.

Figure 2:
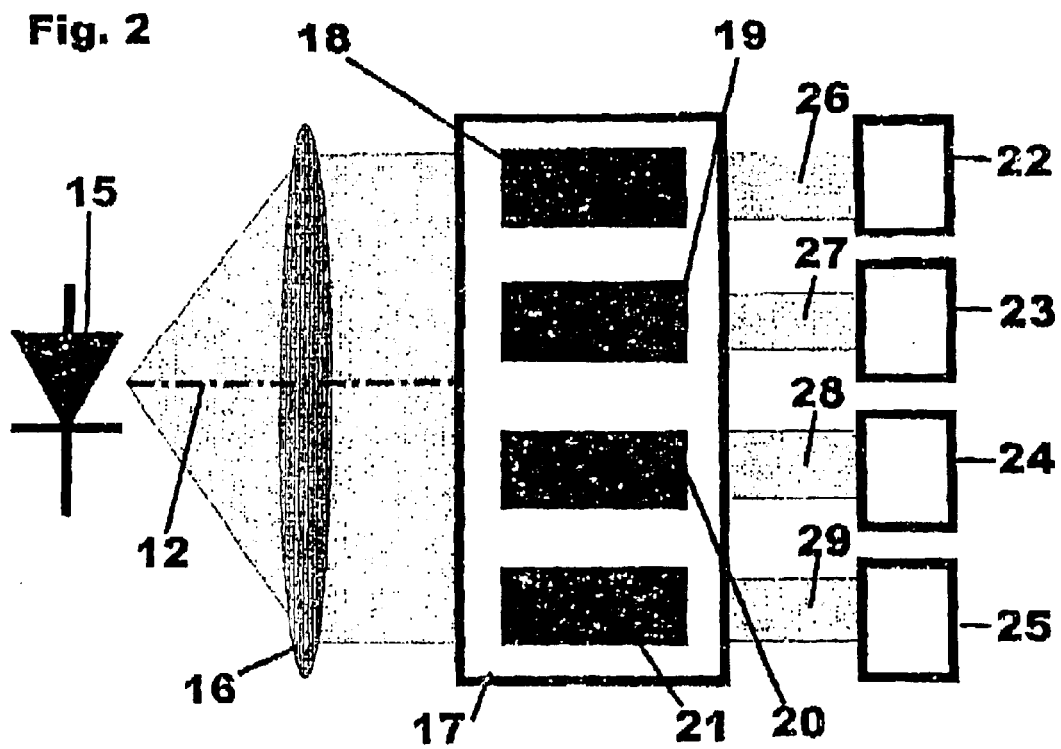
FIG. 2 shows a plasmon resonance sensor with four measurement cells in plan view.

In accordance with the description of FIG. 1, the embodiment according to FIG. 2 provides a laser diode 15, a cylindrical lens 16 and a prism 17, which likewise has a triangular cross section and extends perpendicularly to the incidence plane 12 of the light, with four measurement cells 18, 19, 20 and 21, at which the metal layer 5 and the sensitive coating 6 are respectively present, being formed on the prism 17. Each measurement point is assigned its own detector 22, 23, 24 and 25, respectively.

The incident beam path 10 corresponds to the description with reference to FIG. 1. Accordingly, between the laser diode 15 and the cylindrical lens 16, there is divergence both in the incidence plane 12 and perpendicularly thereto, while, behind the cylindrical lens 16, divergence still takes place only in the incidence plane 12 and there is a parallel beam path perpendicular to the incidence plane. Therefore, the various measurement cells 18 to 21 and the associated detectors 22 to 25 are not only separated from one another but, in particular, are also decoupled from one another in terms of the beams, as illustrated by the emerging beam paths 26, 27, 28 and 29, and this is true even when there is a small distance between the measurement cells 18 to 21, and therefore between the detectors 22 to 25, and despite the divergence present in the emerging beam paths 26 to 29, which, however, only exists in the direction of the incidence plane 12. In this way, a compact arrangement with four measurement cells 18 to 21 can be achieved with only one laser diode 15, one cylindrical lens 16 and one prism 17.

Using the four measurement cells 18 to 21, it is possible to study four samples simultaneously, or, alternatively, to study three samples in conjunction with a reference measurement employing a known reference sample. The increase in performance due to additional measurement cells is particularly advantageous because the individual measurements may be comparatively time-consuming, depending on the samples to be studied, or on the molecules to be detected. For example, especially for biological or biochemical tests, the study or measurement time may respectively be up to one hour.

Figure 3:
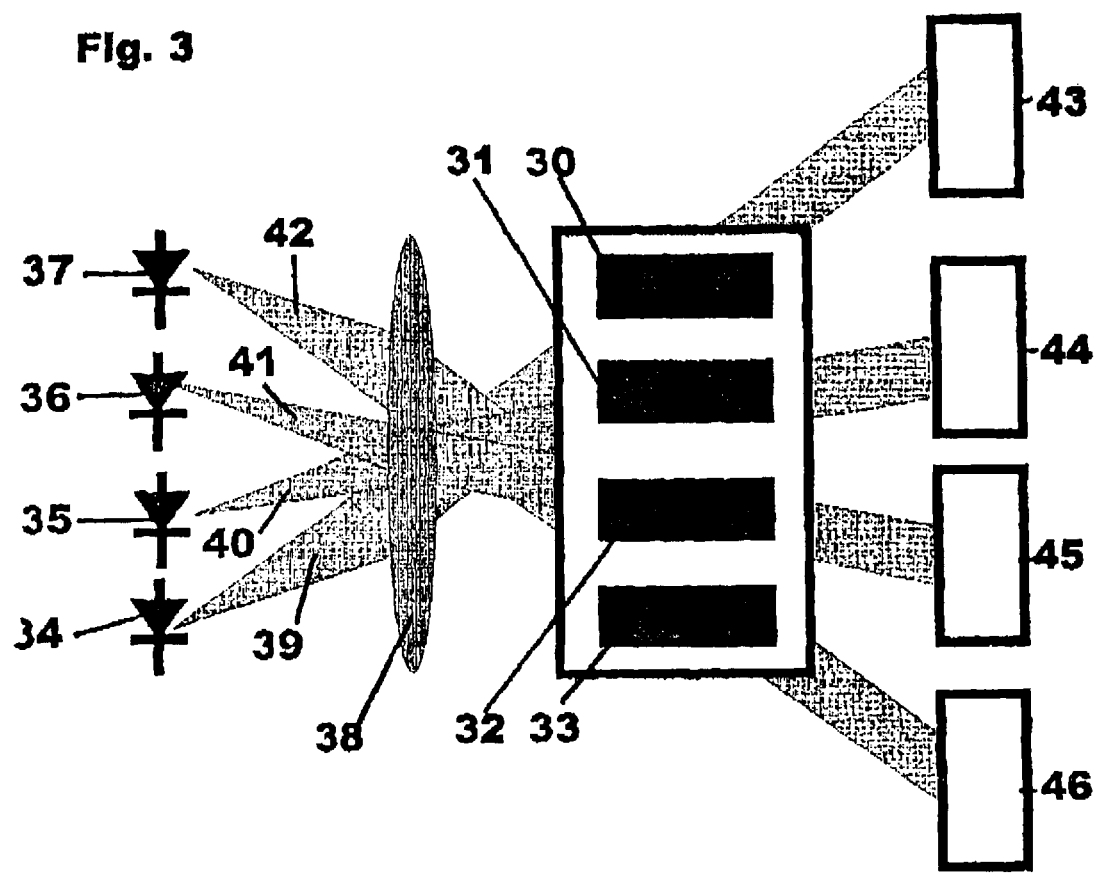
FIG. 3 shows a plasmon resonance sensor which is similar to the embodiment according to FIG. 2, but in which each measurement cell is assigned its own light source.
Figure 4:
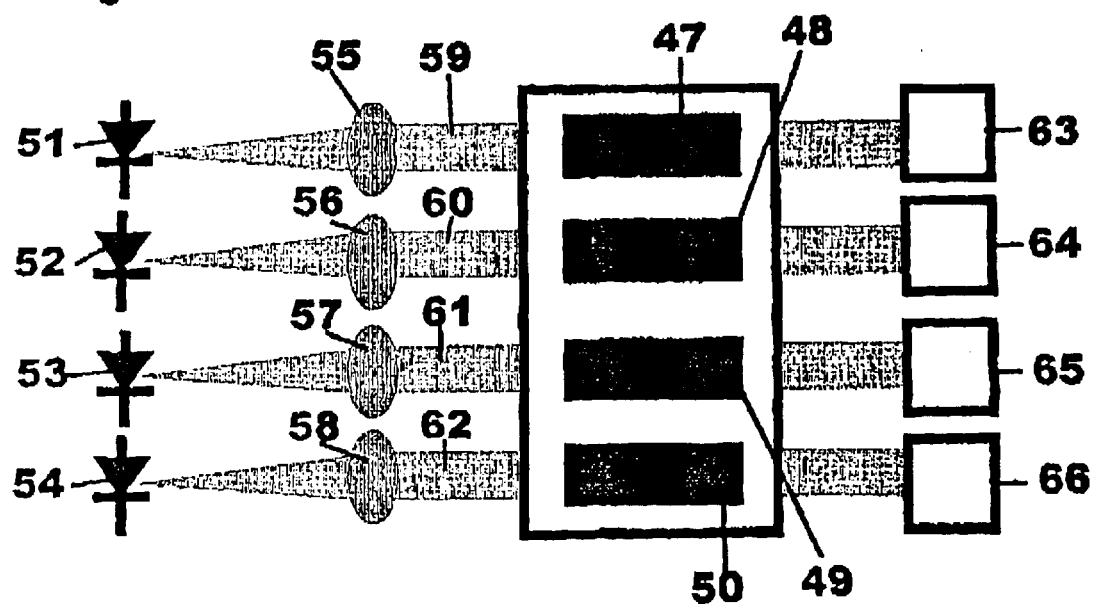
FIG. 4 shows a further variant in relation to the embodiment according to FIG. 3, according to which each measurement cell and light source is assigned its own collimation optics.

The embodiments according to FIG. 3 and FIG. 4 also provide a common prism 17 with four measurement cells, and detectors assigned to them. The differences respectively concern the beam path, although there is no change in terms of the beam divergence in the incidence plane and the collimation in a direction perpendicular to the incidence plane.

According to FIG. 3, the measurement cells 30 to 33 are assigned their own laser diodes 34 to 37. In spite of this, it is possible to operate with a common cylindrical lens 38 which collimates the four differently directed beam paths 39 to 42. Owing to the beam paths 39 to 45 which emerge in a fan-like manner, the arrangement of the detectors 43 to 46 is spread out in a way which occupies somewhat more space.

This can be obviated if, according to FIG. 4, each laser diode 51 to 54 assigned to a measurement cell 47 to 50 is assigned its own cylindrical lens 55 to 58. In the case, the individual beam paths 39 to 62 extend parallel to one another until they strike the detectors 63 to 66 assigned to the measurement cells 47 to 50.

What is claimed is:

1. A plasmon resonance sensor for biological, biochemical or chemical tests, comprising:

an optically transparent body (1, 17), in particular a glass prism;

a reflective metal layer (5) or semiconductor layer which is applied to one face (4) of the body (1, 17) and has a surface (6) sensitive to molecules to be detected in a sample, which forms a measurement cell in conjunction with a cuvette;

a monochromatic light source (7, 15, 34 to 37, 51 to 54), in particular a laser diode, for emitting a divergent light pencil or beam path (9, 26 to 29, 39 to 42, 59 to 82) through the optically transparent body (1, 17) onto the inner face of the layer (5); and a detector (8, 22 to 25, 43 to 46, 63 to 66) which is assigned to the emerging beam path (11) reflected by the layer (5) and registers as a function of time the light emergence angle, which changes as a result of molecule buildup on the sensitive surface (6), at which an emerging light intensity minimum occurs owing to resonance, wherein collimation optics (13, 16, 38, 55 to 58), which collimate the incident beam path (10) perpendicularly to the incidence plan (12) are arranged between the light source (7, 15, 34 to 37, 51 to 54) and the optically transparent body (1, 17), wherein the collimation optics leave the incident beam path (10) divergent in the incidence plane, such that the incident beam path is defocusing, and wherein the optically transparent body (1, 17) is assigned two or more different samples, which are aligned in a row perpendicular to the incidence plane (12).

2. The plasmon resonance sensor as claimed in claim 1, wherein a cylindrical lens is provided as the collimation optics (13, 16, 38, 55 to 58).

3. The plasmon resonance sensor as claimed in claim 1, wherein the sensitive surface is formed by a sensitive coating (6) of the reflective layer (6).

4. The plasmon resonance sensor as claimed in claim 1, wherein each measurement cell is assigned its own detector (22 to 25, 43 to 48, 63 to 66).

5. The plasmon resonance sensor as claimed in claim 4, wherein a signal reflective layer (5) is provided, which extends perpendicularly to the incidence plane (12) over all the measurement cells (18 to 21, 30 to 33, 47 to 50).

6. The plasmon resonance sensor as claimed in claim 4, wherein each measurement cell (30 to 33, 47 to 50) is assigned its own light source (34 to 37, 51 to 54).

7. The plasmon resonance sensor as claimed in claim 6, wherein the light sources (34 to 37) are assigned common collimation optics (38).

8. The plasmon resonance sensor as claimed in claim 6, wherein each light source (51 to 54) is assigned its own collimation optics (55 to 58).

9. The plasmon resonance sensor as claimed in claim 4, wherein the measurement cells are separated from one another by diaphragms.

* * * * *

UNITED STATES PATENT AND TRADEMARK OFFICE
CERTIFICATE OF CORRECTION

PATENT NO. : 6,801,317 B2 Page 1 of 1
DATED : November 1, 2002
INVENTOR(S) : Andreas Hofmann It is certified that error appears in the above-identified patent and that said Letters Patent is hereby corrected as shown below:

<u>Title page,</u>
Item [73], Assignee, should read -- Jandratek Gmbh --

Signed and Sealed this

Twenty-second Day of February, 2005

JON W. DUDAS
*Director of the United States Patent and Trademark Office*